US006979324B2

(12) United States Patent
Bybordi et al.

(10) Patent No.: US 6,979,324 B2
(45) Date of Patent: Dec. 27, 2005

(54) CLOSED WOUND DRAINAGE SYSTEM

(75) Inventors: Farhad Bybordi, Pompano Beach, FL (US); John J. Biggie, Lighthouse Point, FL (US); Lydia B. Biggie, Lighthouse Point, FL (US); John A. Dawson, Dallastown, PA (US)

(73) Assignee: NeoGen Technologies, Inc., Ft. Lauderdale, FL (US)

( * ) Notice: Subject to any disclaimer, the term of this patent is extended or adjusted under 35 U.S.C. 154(b) by 0 days.

(21) Appl. No.: 10/243,004

(22) Filed: Sep. 13, 2002

(65) Prior Publication Data

US 2004/0054338 A1 Mar. 18, 2004

(51) Int. Cl.[7] ............................ A61M 1/00; A61M 27/00
(52) U.S. Cl. ......................... 604/313; 604/327; 604/543
(58) Field of Search .............................. 604/289, 290, 604/313, 543, 327, 355

(56) References Cited

U.S. PATENT DOCUMENTS 765,746 A    7/1904   Miner
843,674 A    2/1907   Funk (Continued)

FOREIGN PATENT DOCUMENTS

DE    561757    10/1932
DE    847475    6/1952

(Continued)

OTHER PUBLICATIONS

Arturson, Gosta M., "The Pathophysiology of Severe Thermal Injury," JBCR, Mar./Apr., 1985, 6(2):129–146.
Clark, R.A.F., et al., The Molecular and Cellular Biology of Wound Repair, Chapter 1 (1988) (33 pages), Plenum Press, New York.

(Continued)

Primary Examiner—Larry I. Schwartz
Assistant Examiner—Michael G. Bogart
(74) Attorney, Agent, or Firm—Jenkens & Gilchrist

(57) ABSTRACT

A portable closed wound drainage system that uses a pouch shaped dressing which is inserted into a wound. At least a portion of the outer surface of the pouch is porous to allow exudates to enter. Exudates are removed from the pouch by flexible tubing which is secured inside the pouch at one end, and secured at the other end to a portable drain/suction unit. The pouch contains porous material, and may optionally contain beads and fillers which are antibacterial in nature. The tubing can have a single or multi-lumen structure with perforations in the side walls of the end of the tube that is inserted in the pouch to allow body fluids to enter laterally. The portable drain/suction unit is preferably a portable battery powered device. The pouch and the tube are sealed by a flexible sealing material which is applied to the outer surface of the skin around the periphery of the pouch and the tubing as it exits the pouch. This sealing material is preferably a hydro-colloid, a silicone, or a lyogel, such as a hydrogel, which are easily deformable. A cosmetic cover sheet is attached to the patient's skin over the closed wound drainage system.

30 Claims, 6 Drawing Sheets

U.S. PATENT DOCUMENTS

| | | | |
|---|---|---|---|
| 1,355,679 A | 10/1920 | McConnell | |
| 1,355,846 A | 10/1920 | Bannells | |
| 1,385,346 A | 7/1921 | Taylor | |
| 2,232,254 A | 2/1941 | Morgan | |
| 2,280,915 A | 4/1942 | Johnson | |
| 2,338,339 A | 1/1944 | Mere et al. | |
| 2,547,758 A | 4/1951 | Keeling | |
| 2,969,057 A | 1/1961 | Simmons | |
| 3,026,526 A | 3/1962 | Montrose | |
| 3,026,874 A | 3/1962 | Stevens | |
| 3,042,041 A | 7/1962 | Jascalevich | |
| 3,367,332 A | 2/1968 | Groves | |
| 3,478,736 A | 11/1969 | Roberts et al. | |
| 3,481,326 A | 12/1969 | Schamblin | |
| 3,486,504 A | 12/1969 | Austin, Jr. | |
| 3,520,300 A | 7/1970 | Flower, Jr. | |
| 3,568,675 A | 3/1971 | Harvey | |
| 3,610,238 A | 10/1971 | Rich, Jr. | |
| 3,648,692 A | 3/1972 | Wheeler | |
| 3,682,180 A | 8/1972 | McFarlane | |
| 3,809,087 A | 5/1974 | Lewis, Jr. | |
| 3,874,687 A | 4/1975 | Barbieri | |
| 3,896,810 A | 7/1975 | Akiyama | |
| 3,908,664 A | 9/1975 | Loseff | |
| 3,954,105 A | 5/1976 | Nordby et al. | |
| 3,993,080 A | 11/1976 | Loseff | |
| RE29,319 E | 7/1977 | Nordby et al. | |
| 4,080,970 A | 3/1978 | Miller | |
| 4,096,853 A | 6/1978 | Weigand | |
| 4,112,947 A | 9/1978 | Nehring | |
| 4,139,004 A | 2/1979 | Gonzalez, Jr. | |
| 4,149,541 A | 4/1979 | Gammons et al. | |
| 4,165,748 A | 8/1979 | Johnson | |
| 4,169,563 A | 10/1979 | Leu | |
| 4,172,455 A | 10/1979 | Beaussant | |
| 4,182,343 A | 1/1980 | Inaba | |
| 4,224,945 A | 9/1980 | Cohen | |
| 4,250,882 A | 2/1981 | Adair | |
| 4,261,363 A | 4/1981 | Russo | |
| 4,275,721 A | 6/1981 | Olson | |
| 4,297,995 A | 11/1981 | Golub | |
| 4,333,468 A | 6/1982 | Geist | |
| 4,373,519 A | 2/1983 | Errede | |
| 4,382,441 A | 5/1983 | Svedman | |
| 4,392,853 A | 7/1983 | Muto | |
| 4,419,097 A | 12/1983 | Rowland | |
| 4,468,227 A | 8/1984 | Jensen | |
| 4,469,092 A | 9/1984 | Marshall et al. | |
| 4,475,909 A | 10/1984 | Eisenberg | |
| 4,480,638 A | 11/1984 | Schmid | |
| 4,525,166 A | 6/1985 | Leclerc | |
| 4,527,064 A | 7/1985 | Anderson | |
| 4,533,352 A * | 8/1985 | Van Beek et al. | 604/317 |
| 4,543,100 A | 9/1985 | Brodsky | |
| 4,551,139 A | 11/1985 | Plaas et al. | |
| 4,553,967 A | 11/1985 | Ferguson et al. | |
| 4,569,348 A | 2/1986 | Hasslinger | |
| 4,573,965 A | 3/1986 | Russo | |
| 4,605,399 A | 8/1986 | Weston et al. | |
| 4,608,041 A * | 8/1986 | Nielsen | 604/23 |
| 4,624,656 A * | 11/1986 | Clark et al. | 604/23 |
| 4,640,688 A | 2/1987 | Hauser | |
| 4,733,659 A | 3/1988 | Edenbaum et al. | |
| 4,743,232 A | 5/1988 | Kruger | |
| 4,759,354 A | 7/1988 | Quarfoot | |
| 4,764,167 A | 8/1988 | Tu | |
| 4,765,316 A | 8/1988 | Marshall | |
| 4,775,909 A | 10/1988 | Inoue et al. | |
| 4,778,456 A | 10/1988 | Lokken | |
| 4,813,094 A * | 3/1989 | Krotine | 15/244.1 |
| 4,820,265 A | 4/1989 | DeSatnick et al. | |
| 4,820,284 A | 4/1989 | Hauri | |
| 4,834,110 A | 5/1989 | Richard | |
| 4,836,192 A | 6/1989 | Abbate | |
| 4,838,883 A | 6/1989 | Matsuura | |
| 4,840,187 A | 6/1989 | Brazier | |
| 4,851,545 A | 7/1989 | Song et al. | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,917,112 A | 4/1990 | Kalt | |
| 4,919,654 A | 4/1990 | Kalt | |
| 4,921,492 A | 5/1990 | Schultz et al. | |
| 4,925,447 A | 5/1990 | Rosenblatt | |
| 4,931,519 A | 6/1990 | Song et al. | |
| 4,936,834 A | 6/1990 | Beck et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,969,881 A | 11/1990 | Viesturs | |
| 4,985,019 A | 1/1991 | Michelson | |
| 5,035,884 A | 7/1991 | Song et al. | |
| 5,037,397 A | 8/1991 | Kalt et al. | |
| 5,045,075 A | 9/1991 | Ersek | |
| 5,086,764 A | 2/1992 | Gilman | |
| 5,100,396 A | 3/1992 | Zamierowski | |
| 5,106,362 A | 4/1992 | Gilman | |
| 5,113,871 A | 5/1992 | Viljanto et al. | |
| 5,149,331 A | 9/1992 | Ferdman et al. | |
| 5,228,431 A | 7/1993 | Giarretto | |
| 5,240,862 A | 8/1993 | Koenhen et al. | |
| 5,261,893 A | 11/1993 | Zamierowski | |
| 5,279,010 A | 1/1994 | Ferrand et al. | |
| 5,298,015 A | 3/1994 | Komatsuzaki et al. | |
| 5,358,494 A | 10/1994 | Svedman | |
| 5,370,610 A | 12/1994 | Reynolds | |
| D364,679 S | 11/1995 | Heaton et al. | |
| 5,527,293 A | 6/1996 | Zamierowski | |
| 5,540,412 A | 7/1996 | Doll | |
| 5,549,584 A * | 8/1996 | Gross | 604/313 |
| 5,618,275 A * | 4/1997 | Bock | 604/290 |
| 5,624,419 A | 4/1997 | Ersek et al. | |
| 5,636,643 A | 6/1997 | Argenta et al. | |
| 5,643,229 A | 7/1997 | Sinaiko | |
| 5,645,081 A | 7/1997 | Argenta et al. | |
| 5,656,588 A | 8/1997 | Zaloga et al. | |
| 5,664,270 A | 9/1997 | Bell et al. | |
| 5,678,564 A | 10/1997 | Lawrence et al. | |
| 5,685,859 A | 11/1997 | Kornerup | |
| 5,686,303 A | 11/1997 | Korman | |
| 5,840,049 A | 11/1998 | Tumey et al. | |
| D406,899 S | 3/1999 | Cottle | |
| 5,891,111 A | 4/1999 | Ismael | |
| 5,906,016 A | 5/1999 | Ferrand et al. | |
| 5,911,222 A | 6/1999 | Lawrence et al. | |
| 5,914,264 A | 6/1999 | Korman | |
| 5,921,972 A * | 7/1999 | Skow | 604/313 |
| 5,926,884 A * | 7/1999 | Biggie et al. | 5/714 |
| 5,931,797 A | 8/1999 | Tumey et al. | |
| 6,056,730 A | 5/2000 | Greter | |
| 6,071,267 A | 6/2000 | Zamierowski | |
| 6,102,935 A | 8/2000 | Harlan et al. | |
| 6,117,111 A | 9/2000 | Fleischmann | |
| D434,150 S | 11/2000 | Tumey et al. | |
| 6,142,982 A | 11/2000 | Hunt et al. | |
| 6,174,306 B1 | 1/2001 | Fleischmann | |
| 6,203,563 B1 | 3/2001 | Fernandez | |
| 6,290,685 B1 | 9/2001 | Insley et al. | |

| | | | |
|---|---|---|---|
| 6,299,593 B1 | 10/2001 | Wakabayashi | |
| 6,345,623 B1 | 2/2002 | Heaton et al. | |
| 6,375,240 B1 | 4/2002 | Lindberg | |
| 6,387,065 B1 | 5/2002 | Tumey | |
| 6,398,767 B1 * | 6/2002 | Fleischmann | 604/313 |
| 6,420,622 B1 | 7/2002 | Johnston et al. | |
| 6,458,109 B1 * | 10/2002 | Henley et al. | 604/304 |
| 6,468,237 B1 | 10/2002 | Lina | |
| 6,493,568 B1 | 12/2002 | Bell et al. | |
| 6,500,112 B1 | 12/2002 | Khouri | |
| D469,175 S | 1/2003 | Hall et al. | |
| D469,176 S | 1/2003 | Hall et al. | |
| 6,551,280 B1 | 4/2003 | Knighton et al. | |
| 6,553,998 B2 | 4/2003 | Heaton et al. | |
| D475,132 S | 5/2003 | Randolph | |
| D475,134 S | 5/2003 | Randolph | |
| 6,557,704 B1 | 5/2003 | Randolph | |
| D478,659 S | 8/2003 | Hall et al. | |
| 6,620,132 B1 * | 9/2003 | Skow | 604/131 |
| 6,626,891 B2 * | 9/2003 | Ohmstede | 604/543 |
| 6,641,527 B2 | 11/2003 | Khouri | |
| 6,641,575 B1 | 11/2003 | Lonky | |
| 6,663,610 B1 * | 12/2003 | Thompson et al. | 604/313 |
| 6,695,823 B1 | 2/2004 | Lina et al. | |
| 2001/0029956 A1 | 10/2001 | Argenta et al. | |
| 2002/0143286 A1 | 10/2002 | Turney | |
| 2002/0161346 A1 * | 10/2002 | Lockwood et al. | 604/315 |
| 2003/0050594 A1 | 3/2003 | Zarnierowski | |
| 2004/0039415 A1 | 2/2004 | Zarnierowski | |

FOREIGN PATENT DOCUMENTS

| | | |
|---|---|---|
| DE | 2809828 | 9/1978 |
| DE | 41 11 122 A1 | 4/1993 |
| EP | 0 620 720 B1 | 3/1998 |
| EP | 0 688 189 B1 | 9/2000 |
| GB | 641061 | 8/1950 |
| GB | 1273342 | 5/1972 |
| GB | 2125296 A | 3/1984 |
| JP | 1005548 A2 | 1/1989 |
| WO | WO90/11795 | 10/1990 |
| WO | WO91/00718 | 1/1991 |
| WO | WO91/16030 | 10/1991 |
| WO | WO92/19313 | 11/1992 |
| WO | WO92/20299 | 11/1992 |
| WO | WO 93/09736 * | 5/1993 ............. A61F/5/44 |
| WO | WO94/20041 | 9/1994 |
| WO | WO96/05873 | 2/1996 |

OTHER PUBLICATIONS

Mulder, G.D., et al., Clinician's Pocket Guide to Chronic Wound Repair, 1991, pp. 54–55, Wound Healing Publications, Spartanburg, SC.

Chariker, M.E. et al., "Effective Management of Incisional and Cutaneous Fistulae with Closed Suction Wound Drainage," Contemporary Surgery, Jun., 1989, pp. 59–63, vol. 34.

Jeter, K.F. et al. "Managing Draining Wounds and Fistulae: New and Established Methods," Chronic Wound Care: Health Management Publications, 1990, pp. 240–246.

"What's So Special About the Moblvac II Portable Suction System?", Aeros, (1 page).

"Care–E–Vac", Aeros, Aug. 1993 (2 pages).

"Emerson Post–Operative Suction Pumps", Emerson, Series 55. J.H. Emerson Co., Cambridge, MA, (1 page).

"Emerson Transport Suction Unit", Emerson, J.H. Emerson Co., Cambridge, MA, (1 page).

"Instavac Aspirator", Aeros, Aeros Instruments, Inc., Northbrook, IL Oct. 1988, Part No. 1504–02 7M. (1 page).

"Pleur–evac. Adult–Pediatric, Non–Metered." Code No. A–4000. Control No. F7961J (5 pages).

"TUGS (Transportable Universal Gradient Suction", Instruction Manual, Creative Medical Laboratories, Inc., Rochester, Minn. (7 pages).

"Pleur–evac", Deknatel, Div. of Howmedica, Inc. Queens Village, NY (1 page).

"Power Source Multi–Purpose Surgical Aspirator" Sparta Instrument Corp., Hayward, CA (1 page).

"Point 5 Aspirator", Wells Johnson Company, Tucson, AZ (2 pages).

"Wound–Evac ET Closed Wound Suction System", Microtek Heritage, Columbus, MS, No. 0012 (4 pages).

Fleischmann, W., Wund Forum Spezial. IHW '94. "Vakuumversiegelung zur Behandlung von Problemwunden" (with English translation: Vacuum Sealing for Treatment of Problematical Wounds) (7 pages).

Fleischmann, W., "Treatment of Bone and Soft Tissue Defects in Infected Nonunion", Acta Orthopaedica Belgica Suppl. 1–1992, vol. 58 (9 pages).

Fleischmann, W., "Vakuumversiegelung zur Behandlung des Weichteilschadens bei offenen Frakturen." (English abstract, no English translation) (5 pages) Unfall Chirurg. Springer–Varlag (1993).

Valenta, A., "Using the Vacuum Dressing Alternative for Difficult Wounds", American Journal Of Nursing, Apr. 1994 (2 pages).

Letsou et al. "Stimulation of Adenylate Cyclase Activity in Cultured Endothelial Cells Subjected to Cyclic Stretch." J Cardiovascular Surgery 31. Toronto. Sep. 1990 (pp. 634–639).

Bucalo et al. "Inhibition of Cell Proliferation by Chronic Wound Fluid." Wound Repair and Regeneration. Jul.–Sep. 1993 (pp. 181–186).

Falanga, Vincent. "Growth Factors and Chronic Wounds: The Need to Understand the Microenvironment." Journal of Dermatology, vol. 19, 1992 (pp. 667–672).

Urschel et al. "The Effect of Mechanical Stress on Soft and Hard Tissue Repair; a Review." British Journal of Plastic Surgery, 1988 vol. 41 (pp. 182–186).

Gogia, Prem P. "The Biology of Wound Healing." Ostomy/Wound Management. Nov.–Dec. 1992. pp. 12–20.

Olenius et al., "Mitotic Activity in Expanded Human Skin." Plastic and Reconstructive Surgery. Feb. 1993, pp. 213–215, vol. 91, No. 2.

Rastgeldi, S., "I. Pressure Treatment of Peripheral Vascular Diseases. II. Intermittent Pressure Treatment of Peripheral Vascular Diseases.", Opuscula Medica, Suppl. XXVII, 1972 (49 pages).

Author Unknown, "Hyperemia by Suction Apparatus", Chapter VIII, pp. 74–85.

Saunders, J.W., "Negative–Pressure Device for Controlled Hypotension During Surgical Operations", The Lancet, Jun. 28, 1952, pp. 1286–1287.

Landis et al., "The Effects of Alternate Suction and Pressure on Blood Flow to the Lower Extremities," Robinette Foundation of the Hospital of the University of Pennsylvania, (pp. 925–961).

Hargens et al., "Control of Circulatory Functions in Altered Gravitational Fields" Space Physiology Laboratory, Life Science Division, NASA, Ames Research Center (4 pages).

Wolthuis et al., "Physiological Effects of Locally Applied Reduced Pressure in Man", Physiological Reviews, Jul., 1974, 54:566–595.

Viljanto et al., "Local hyperalimentation to open wounds", Br J Surg., 1976, 63:427–430.

Dillon, "Treatment of Resistant Venous Stasis Ulcers and Dermatitis with the End–Diastolic Pneumatic Compression Boot", Angiology—The Journal of Vascular Diseases, Jan. 1986, pp. 47–55.

Lundvall et al., "Transmission of externally applied negative pressure to the underlying tissue. A study on the upper arm of man", Acta Physiol Scand, 136: 403–409, accepted Jan. 28, 1989.

Klemp et al., "Subcutaneous Blood Flow in Early Male Pattern Baldness", The Journal of Investigative Dermatology, 1989, pp. 725–726.

A. Harle, "Schwachstellen herkommlicher Drainagen", Z. Orthop., 1989, 127: 513–517.

Dunlop et al., "Vacuum drainage of groin wounds after vascular surgery: a controlled trial", Br. J. Surg., 1990, 77: 562–563.

Maddin et al., "The Biological Effects of a Pulsed Electrostatic Field with Specific Reference to Hair: Electrotrichogenesis", International Journal of Dermatology, 1990, 29: 446–450.

Nakayama et al., "A New Dressing Method for Free Skin Grafting in Hands", Ann. Plast. Surg., 1991, 26: 499–502.

Hargens et al., "Lower Body Negative Pressure to Provide Load Bearing in Space", Aviation, Space and Environmental Medicine, Oct. 1991, pp. 934–937.

Author unknown, "The Not–So–Bald–Truth", Science, p. 42 (1 page).

"HiBlow Air Pump", Techno Takatsuki Co., Ltd., Osaka, Japan (1 page).

"Wells Johnson Suction Tips", American Journal Of Nursing, Apr. 1994 (1 page).

"Miscellaneous Equipment" IEN Industrial Equipment News, Skokie, IL, (1 page).

Wysocki et al., "Wound Fluid from Chronic Leg Ulcers Contains Elevated Levels of Metalloproteinases MMP-2 and MMP-9." The Society for Investigative Dermatology, Inc., Jul. 1993 (pp. 64–68).

Finley, John M., M.D., "Subclavian Intravenous Catheters", Manual of Wound Dressings, pp. 124–148.

Fleck, et al., "When Negative is Positive: A Review of Negative Pressure Wound Therapy," For submission to the Mar./Apr. 2004 ECPN Wound Care Column (12 pages).

Philbeck Jr., et al., "The Clinical and Cost Effectiveness of Externally Applied Negative Pressure Wound Therapy in the Treatment of Wounds in Home Healthcare Medicare Patients", Ostomy/Wound Management, Jan. 1999; 45(11):41–50.

Murphy et al., "Options in Practice: Care of An Obese Patient with a Pressure Ulcer," 2001, JWOCN, 28:171–6.

Morykwas,, Michael et al., "Vacuum–Assisted Closure: A New Method for Wound Control and Treatment: Animal Studies and Basic Foundation," Annals of Plastic Surgery, Jun. 1997, vol. 38, No. 6 (6 pages).

Mendes–Eastman, Susan, "Negative Pressure Wound Therapy," Plastic Surgical Nursing, Spring 1988, vol. 18, No. 1, pp. 27–29, 33–37.

Schneider, Andrew, et al., "A New and Reliable Method of Securing Skin Grafts to the Difficult Recipient Bed," Plastic and Reconstructive Surgery, Sep. 1998, vol. 102, No. 4 (2 pages).

Rohrich, Rod J. et al., "An Algorithm for Abdominal Wall Reconstruction," Plastic and Reconstructive Surgery, Jan. 2000, vol. 105, No. 1 (8 pages).

Obdeijn, Miryam C. et al., "Vacuum–Assisted Closure in the Treatment of Poststernotomy Mediastinitis," Ann. Thoracic Surgery, 1999; 68:2358–60.

Morykwas, Michael J. et al., "Nonsurgical Modalities to Enhance Healing and Care of Soft Tissue Wounds," Journal of the Southern Orthopedic Association, Winter 1997, vol. 6, No. 4, pp. 279–288.

Meara, John G. et al., "Vacuum–Assisted Closure in the Treatment of Degloving Injuries," Annals of Plastic Surgery, Jun. 1999, vol. 42, No. 6 (pp. 589–594).

Molnar ,Joseph A. et al, "Single–Stage Approach to Skin Grafting the Exposed Skull," Plastic and Reconstructive Surgery, Jan., 2000, vol. 105, No. 1 (pp. 174–177).

Joseph, Emmanuella et al, "A Prospective Randomized Trial of Vacuum–Assisted Closure Versus Standard Therapy of Chronic Nonhealing Wounds," Wounds 2000; 12(3):60–67.

Greer, Steven E. et al., "Techniques for Applying Subatmospheric Pressure Dressing to Wounds in Difficult Regions of Anatomy," JWOCN, Sep. 1999, vol. 26, No. 5, (pp. 250–253.

ConstaVac™ Closed Wound Drainage System, Stryker Instruments (2 pages).

Serry, Cyrus, et al., "Sternal Wound Complications: Management and Results," J Thorac Cardiovasc Surg, 1980, 80:861–867.

Tang, A.T.M., et al., "Vacuum–Assisted Closure to Treat Deep Sternal Wound Infection Following Cardiac Surgery," Journal of Wound Care, May 2000, vol. 9, No. 5 (3 pages).

Argenta, Louis C. et al., "Vacuum–Assisted Closure: A New Method for Wound Control and Treatment: Clinical Experience," Annals of Plastic Surgery, Jun. 1997, vol. 38, No. 6 (15 pages).

Putney, F. Johnson, M.D., "The Use of Continuous Negative Pressure After Laryngectomy and Radical Neck Dissection," Surgery, Jul. to Dec. 1956, vol. 103 (5 pages).

Fay, Margaret F., "Drainage Systems—Their Role in Wound Healing," Aorn Journal, Sep. 1987, vol. 46, No. 3 (10 pages).

Fox, James W. et al. "The Use of Drains in Subcutaneous Surgical Procedures," The American Journal of Surgery, Nov. 1976, vol. 132 (3 pages).

Sames, C. Patrick, "Sealing of Wounds With Vacuum Drainage" (1 page).

Davis, T.P., "The Advantages of Suction Drainage in Surgical Wounds," The Medical Journal of Australia, Feb. 1, 1958 (3 pages).

Hartz, Renee S. et al., "Healing of the Perineal Wound," Arch Surg. Apr. 1980, vol. 115 (5 pages).

Morris, A. M., "A Controlled Trial of Closed Wound Suction, Drainage in Radical Mastectomy," The British Journal of Surgery, Jan. 1973 to Dec. 1973, vol. 60 (4 pages).

Berman, Arnold T., et al., "Comparison Between Intermittent (Spring–Loaded) and Continuous Closed Suction Drainage of Orthopedic Wounds: A Controlled Clinical Trial," Orthopedics, Mar. 1990 vol. 13/No. 3 (8 pages).

McFarlane, R. M., "The Use of Continuous Suction Under Skin Flaps," British Journal of Plastic Surgery, 1958–59, vol. XI (12 pages).

Sutton, Warren T. et al., "Suction for Postoperative Wounds," Archives of Surgery, Jan. through Jun., 1961, vol. 82, (8 pages).

Lesser, Arthur J., "The Place of Wound Drainage in Surgery with Description of a New Drain," Archives of Surgery, Dec. 1960, vol. 81, No. 6 (9 pages).

Sheppard, M. D. et al., "Sealed Drainage of Wounds," The Lancet, Jan.–Jun. 1952, vol. One (5 pages).

Ramirez, Oscar M. et al., "Optimal Wound Healing Under Op–Site Dressing," Plastic and Reconstructive Surgery, Mar. 1984, vol. 73, No. 3 (3 pages).

Silvis, Richard S. et al., "The Use of Continuous Suction Negative Pressure Instead of Pressure Dressing," Annals of Surgery, Jul.–Dec. 1955, vol. 142 (7 pages).

Giovannini, Uberto M., et al., "Interest of Negative Pressure Therapy in the Treatment of Postoperative Sepsis in Cardiovascular Surgery," Wounds, 2001, Health Management Publications, 13(2):82–87. (7 pages).

Kostiuchenok, B. M., et al., "The Vacuum Effect in the Surgical Treatment of Purulent Wounds," Russian Journal, Vestnik Khirurgii, Sep., 1986 (pp. 18–21).

Davydov, Yu A., et al., "Vacuum Therapy in the Treatment of Purulent Lactation Mastitis," Russian Journal, Vestnik Khirurgii, Sep., 1986, (pp. 66–70).

Usupov, Y.N. et al., "Active Wound Drainage," Russian Journal, Vestnik Khirurgii, Apr., 1987 (pp. 42–45).

Davydov, Yu A., et al., "The Bacteriological and Cytological Assessment of Vacuum Therapy of Purulent Wounds," Russian Journal, Vestnik Khirurgii, Oct., 1988, (pp. 48–52).

Davydov, Yu A., et al., "Concepts for Clinical Biological Management of the Wound Process in the Treatment of Purulent Wounds Using Vacuum Therapy," Russian Journal, Vestnik Khirurgii, Feb., 1991 (pp. 132–135).

Healy DA., et al., "Prophylactic closed suction drainage of femoral wounds in patients undergoing vascular reconstruction," Journal of Vascular Surgery, Aug., 1989, 10(2):166–8 (Abstract–1 page).

Davydov IA, et al., "Vacuum therapy of acute supportive diseases of soft tissues and suppurative wounds," Vestnik Khirurgii Imeni i—i—Grekova. Sep. 1988, 141(9):43–6 (Abstract–1 page).

Tadych K., et al., "Postmastectomy seromas and wound drainage," Surgery, Gynecology & Obstetrics, Dec. 1987, 165(6):483–7 (Abstract–1 page).

Iusupov IN, et al., "Active drainage of a wound," Vestnik Khirurgii Imeni i—i—Grekova. Apr., 1987, 138(4):42–6 (Abstract–1 page).

Hendrich V. et al., "Suction–drainage in the treatment of chronic osteomyelitis," Unfallchirurgie. Apr., 1986, 12(2):101–3 (Abstract–1 page).

Harle A., "Postoperative wound suction drainage and its effect on wound healing," Zeitschrift fur Orthopadie und Ihre Grenzgebiete. May–Jun. 1985, 123(3):395–402 (Abstract–1 page).

Smith, Sr., et al., "Surgical drainage," British Journal of Hospital Medicine, Jun. 1985, 33(6):308, 311, 314–15 (Abstract–1 page).

Lokhvitski SV. Bil'Kevich AA., "[Treatment of carbuncles]," Vestnik Khirurgii Imeni i—i—Grekova, Jan., 1984 132(1):71–4 (Abstract–1 page).

Harle, A., "Weakness of conventional drainage systems," Zeitschrift fur Orthopadie und Ihre Grenzgebiete, Jul.–Aug. 1989, 127(4):513–7 (Abstract–1 page).

Durandy Y., et al., "Mediastinal infection after cardiac operation. A simple closed technique." Journal of Thoracic & Cardiovascular Surgery, Feb. 1989, 97(2):282–5 (Abstract–1 page).

Healy DA, et al., "Prophylactic closed suction drainage of femoral wounds in patients undergoing vascular reconstruction." Journal of Vascular Surgery, Aug., 1989, 10(2):166–8 (Abstract–1 page).

Gerngross H., et al., "Gravity drainage versus suction drainage: an experimental and clinical study." Unfallchirug. Jan. 1989, 92(1):37–42 (Abstract–1 page).

Draca, P., et al., "Extraperitoneal transabdominal vacuum drainage of the parametrial cavity and suprapubic drainage of the urinary bladder after radical hysterectomy." Jugoslavenska Ginekilogija i Perinatologija, May–Aug., 1989, 29(3–4):129–32 (Abstract–1 page).

Willett KM., et al., "The effect of suction drains after total hip replacement." Journal of Bone & Joint Surgery, Aug. 1988, British vol. 70(4):607–10 (Abstract–1 page).

Tittel K., et al., "VariDyne—new standards in postoperative wound drainage." Unfallchirurgie. Apr. 1988, 14(2):104–7 (Abstract–1 page).

Davydov IA., et al., "Vacuum therapy of acute suppurative diseases of soft tissues and suppurative wounds." Vestnik Khirurgii Imeni i—i—Grekova., Sep. 1988, 141(9):43–6 (Abstract–1 page).

Tadych K., et al., "Postmastectomy seromas and wound drainage." Surgery, Gynecology & Obstetrics, Dec. 1987, 165(6):483–7 (Abstract—1 page).

Moss AL., "The DIY mini suction drain." British Journal of Plastic Surgery, Sep. 1987, 40(5):542–3 (Abstract–1 page).

Iusupov IN, et al., "Active drainage of a wound." Vestnik Khirurgii Imeni i—i—Grekova. Apr., 1987, 138(4):42–6 (Abstract–1 page).

Orr JW., et al., "Closed suction pelvic drainage after radical pelvic surgical procedures." American Journal of Obstetrics & Gynecology, Oct. 1986, 155(4):867–71 (Abstract–1 page).

Svedman P., et al., "A dressing system providing fluid supply and suction drainage used for continuous or intermittent irrigation." Annals of Plastic Surgery, Aug. 1986, 17(2):125–33 (Abstract–1 page).

Nasser NA., "The use of the Mini–Flap wound suction drain in maxillofacial surgery." Annals of the Royal College of Surgeons of England., May 1986, 68(3):151–3 (Abstract–1 page).

Hendrich V., et al., "Suction–drainage in the treatment of chronic osteomyelitis." Unfallchirurgie, Apr. 1986, 12(2):101–3 (Abstract–1 page).

Diament MJ., et al., "Percutaneous aspiration and catheter drainage of abscesses." Journal of Pediatrics, Feb. 1986, 108(2):204–8 (Abstract–1 page).

Chinn SD, et al., "Closed wound suction drainage." Journal of Foot Surgery, Jan.–Feb., 1985, 24(1):76–81 (Abstract–1 page).

Harle A., "Postoperative wound suction drainage and its effect on wound healing." Zeitschrift fur Orthopadie and Ihre Grenzgebiete, May–Jun. 1985, 123(3):395–402 (Abstract—1 page).

Pruett TL., et al., Percutaneous aspiration and drainage for suspected abdominal infection. Surgery, Oct. 1984, 96(4):731–7 (Abstract–1 page).

Smith SR., et al., "Surgical drainage." British Journal of Hospital Medicine, Jun. 1985, 33(6): 308, 311, 314–15 (Abstract–1 page).

Kawashima M., et al., "A new instrument for closed irrigation–suction treatment." Nippon Seikeigeka Gakkai Zasshi—Journal of the Japanese Orthopedic Association, Jun. 1983, 57(6):643–50, (Abstract–1 page).

Vergeret J., et al., "Endocavitary drainage (Monaldi's technic) in the treatment of pulmonary abscess." Revue Francaise des Maladies Respiratoires, 1983, 11(3):201–7 (Abstract–1 page).

Vatanasapt V., et al., "Red rubber bulb, cheap and effective vacuum drainage." Journal of the Medical Association of Thailand, Apr. 1989, 72(4):193–7 (Abstract–1 page).

Tittel K., et al., "Vari–Dyne—new standards in postoperative wound drainage." Unfallchirurgie. Apr. 1988, 14(2):104–7 (Abstract–1 page).

Rudberg C., et al., "How does the increasing filling of the vacuum source diminish the suction in modern portable drainage systems?" Acta Chirurgica Scandinavica, Jan. 1988, 154(1):1–8 (Abstract–1 page).

Cooper AJ., "Preliminary experience with a vacuum constriction device (VCD) as a treatment for impotence." Journal of Psychosomatic Research, 1987, 31(3):413–8 (Abstract–1 page).

Hedges JR., et al., "Evaluation of venous distension device: potential aid for intravenous cannulation." Annals of Emergency Medicine, May 1986, 15(5):540–3 (Abstract–1 page).

Ramirez OM., et al., "Optimal wound healing under Op–Site dressing." Plastic & Reconstructive Surgery, Mar. 1984, 73(3):474–5 (Abstract–1 page).

Hollender L.F., et al., "Suction drainage in general and digestive surgery. Apropos of the use of Reliavac material." Journal de Chirurgie, Aug.–Sep., 1984, 121(8–9):539–40 (Abstract–1 page).

Nakayama Y, et al., "A new dressing for free skin grafting in hands." Ann Plast Surg May 1991;26(5):499–502 (Abstract–1 page).

Fay MF., "Drainage systems. Their role in wound healing." AORN J Sep. 1987;46(3):442–55. (Abstract–1 page).

Durandy Y, et al., "Mediastinal infection after cardiac operation. A simple closed technique." J Thorac Cardiovasc Surg, Feb., 1989, 97(2):282–5. (Abstract–1 page).

Berger, DL., "Use of drains in foot surgery." J Foot Surg., May–Jun. 1988; 27(3):245–7. (Abstract–1 page).

Insupov IUN, et al., "Active drainage of a wound." Vestn Khir Im I I Grek, Apr. 1987, 138(4):42–6 (Abstract–1 page).

Fox JW 4$^{TH}$, et al., "The use of drains in subcutaneous surgical procedures." Am J Surg., Nov., 1976, 132(5):673–4. (Abstract–1 page).

Bourke JB, et al., "A comparison between suction and corrugated drainage after simple mastectomy: a report of a controlled trial." Br J Surg., Jan. 1976, 631(1):67–9. (Abstract–1 page).

Chinn SD, et al., "Closed wound suction drainage." J Foot Surg., Jan.–Feb. 1985, 24(1):76–81 (Abstract–1 page).

Guharay BN, et al., "The pacemaker–twiddler's syndrome: another disadvantage of abdominal implantation of pulse generators." Br J Surg., Sep., 1977, 64(9):655–60. (Abstract–1 page).

Elliot MS, et al., "Management of the perineal wound with constant irrigation and suction after abdominoperineal excision for cancer of the rectum. A new suction/irrigation drain." S Afr Med J., Nov. 10, 1979, 56(20):796–98. (Abstract–1 page).

Brummelkamp WH, et al. "Primary closure of the perineum and vacuum drainage after abdominoperineal excision.", Acta Chir Belg., Sep.–Oct. 1983, 83(5)358–64 (Abstract–1 page).

Garcia–Rinald R., et al., "Improving the Efficiency of Wound Drainage Catheters.", Am J Surg., Sep., 1975, 130(3):372–3 (Abstract—1 page).

McCormack T.T., et al., "Abdominal drainage following cholecystectomy: high, low, or no suction?", Ann R Coll Surg., England, Sep. 1983, 65(5):326–8 (Abstract—1 page).

Saha SK, et al., "A Study of Perineal Wound Healing After Abdominoperineal Resection.", Br J Surg., Jul., 1976, 63(7):555–8 (Abstract—1 page).

Werner, H.P., "Complications and Risks of Suction Drainage.", Z Gesamte Hyg,, Feb., 1990, 36(2):94–9 (Abstract—1 page).

Azad, S. et al., "Topical Negative Pressure May Help Chronic Wound Healing", BMJ May 4, 2002; 324:1100 (2 pages).

Author Unknown, "Three Techniques to Save the Lives of Children with Burns, to Close Wounds and Restore Walking Ability.", British Association of Plastic Surgeons, Press Release—Dec. 1996 (3 pages).

Chariker–Jeter® Wound Drainge Kit, Blue Medical, La Costa, California (1 page).

Wooding–Scott® Drainage/Irrigation Kit, Blue Sky Medical, La Costa, California (1 page).

Rosser, Charles, et al., "A New Technique to Manage Perineal Wounds", Infections in Urology, Mar./Apr. 2000 ( 2 pages).

The V.A.C. Vacuum Assisted Closure, The V.A.C. System, KCI, San Antonio, Texas (4 pages).

V.A.C. Recommended Guidelines for Use, Physician and Caregiver Reference Manual, KCI, San Antonio, Texas (20 pages).

Mini V.A.C. Vacuum Assisted Closure Summary Sheet; KCI, San Antonio, Texas (2 pages).

The V.A.C.® System, The Truth About Misuse . . . , KCI, San Antonio, Texas (2 pages).

V.A.C.® Operations Summary, May 2001, KCI, San Antonio, Texas (2 pages).

V.A.C.® Soft–Foam, Aug. 2001, KCI, San Antonio, Texas (2 pages).

The V.A.C. Patient and Family Handbook, KCI, San Antonio, Texas (21 pages).

Excerpts from Articles Published on the V.A.C.® Device, 2001, KCI, San Antonio, Texas (1 page).

Mendez–Eastman, Susan, "When Wounds Won't Heal", RN, Jan. 1998 (4 pages).

"Wound VAC good for some home health patients, but costly for others,", www.myhomehealth.com, Mar. 29, 2002 (3 pages).

Argenta, Louis C. et al., "V.A.C.® Wound Closure Device Case Study #1.", KCI Therapeutic Services, Inc., San Antonio, Texas Apr., 1998 (1 page).

Argenta, Lousi C. et al., "The V.A.C.® Case Study #2", 1995 Kinetic Concepts, Inc. (1 page).

Argenta, Louis C. et al., "V.A.C.® Wound Closure Device Case Study #3,", KCI Therapeutic Services, Inc., San Antonio, Texas, Apr., 1998 (1 page).

Argenta, Louis C. et al., "The V.A.C.® Case Study #4", 1995 Kinetic Concepts, Inc. (1 page).

Argenta, Louis C. et al., "V.A.C.® Wound Closure Device Case Study #5", KCI Therapeutic Services, Inc., San Antonio, Texas, Apr., 1998 (1 page).

"V.A.C.® Wound Closure Device Case Study #6". KCI Therapeutic Services, Inc., San Antonio, Texas, Apr., 1998 (1 page).

"The V.A.C.® Case Study #7", KCI Therapeutic Services, Inc., San Antonio, Texas, 1996 (1 page).

"V.A.C.® Wound Closure Device Case Study #8", KCI Therapeutic Services, Inc., San Antonio, Texas, Apr. 1998 (1 page).

"The V.A.C.® Case Study #10", Kinetic Concepts, Inc., 1996 (1 page).

V.A.C.® Wound Closure Device Case Study #11, 1998 KCI Therapeutic Services, Inc., San Antonio, Texas, Apr. 1998 (1 page).

Harkiss, K. J., "Surgical Dressings and Wound Healing", 1971 Bradford University Press and Crosby Lockwood & Son Ltd., (13 pages).

* cited by examiner

CLOSED WOUND DRAINAGE SYSTEM

BACKGROUND OF THE INVENTION

1. Technical Field

The present invention relates to wound dressings. In particular, it relates to wound dressings which are inserted directly into open wounds and which are combined with a suction system that provides for enhanced drainage of the wound to facilitate rapid healing. The device includes a sealant to provide a leak proof seal around the periphery of the dressing. In addition, optional antibacterial agents are used by the dressing to aid healing.

2. Background Art

The treatment of wounds has resulted in the development of a variety of methods to facilitate healing. One popular technique has been to use negative pressure therapy ("NPT"), which is also known as suction or vacuum therapy. This treatment has been practiced for many years in a wide variety of locations (e.g., Europe, the Middle East, and even ancient China). A variety of NPT devices have been developed to allow exudates (i.e., body secretions) to be removed while at the same time isolating the wound to protect it so that its recovery time is reduced.

A more recently developed form of NPT is known as vacuum assisted closure ("VAC") techniques. The use of VAC techniques in the treatment of wounds is based on the premise that when controlled negative pressure is applied to a wound, it stimulates mitosis, which forms new vessels and closes the wound. Studies have shown that this treatment assists wound healing by providing a moist protective environment, by reducing peripheral edema around the wound, by stimulating circulation to the wound bed, by decreasing bacterial colonization, and by increasing the rate of granulation tissue formation and epithelialization.

NPT is useful in the treatment of a variety of wound types, including acute, subacute, chronic, traumatic, graphs, flaps, pressure ulcers, and diabetic ulcers. NPT has been shown to facilitate healing in deep wounds or cavity wounds due to its vacuum characteristics. In particular, it allows the dead tissue, debris, and/or exudates to be drawn from the wound area under vacuum pressure which increases the rate of healing.

Several other methods of wound draining, in addition to the NPT and VAC, methods discussed above, are known. For example, suction therapy, drain therapy, electrical simulation, and even the use of leaches. All of these techniques are directed to the same goal, which is the removal of dead tissue, exudates, and any other contaminants in a wound.

These methods use devices that have been developed for use in treatment of a variety of wound types, including cuts, burns, and other injuries. They typically include a watertight seal over the wound. Generally, the watertight seal is adhered to the portion of the outer skin which surrounds the wound area. By forming a watertight seal, contaminants are prevented from accessing the wound and fluids accumulating in the wound area are prevented from leaking through the wound dressing. Isolation of the wound therefore helps not only the recovery process, but also prevents exposure of contaminated exudates to others. However, the production of body fluids during healing process creates a problem and that they interfere with the healing process if they are allowed to accumulate. As a result, a number of devices have been developed to assist drainage in the wound area for the purpose of aiding the body during natural healing process.

One type of wound dressing uses a porous foam insert which is inserted into a wound. Typically, a drainage tube, a drainage pump, and a dressing cover are combined with the porous foam insert to form a system which siphons exudates from the wound. There are problems associated with this type of dressing. For example, because the foam has a memory as to its shape, it may leave gaps inside the wound cavity rather than filling the entire cavity. Likewise, since the drainage tube extends from the porous foam insert through the dressing cover, if the drainage cover is not adequately sealed in the area where the drainage tube exits, then there can be leakage in either direction. If this occurs, the wound is subject to contamination, and the exudates which leak out may expose others to infection. Further, the more an individual patient moves about, the more likely it is that this type of wound dressing will fail and create leakage. It would be desirable to have a wound dressing which is capable of filling the wound cavity, sealing a wound in the location of the drainage tube, and maintaining a leak proof seal when the patient is mobile.

Another type of dressing has been developed which uses a flexible single piece dressing that has a unitary structure which combines a drainage tube as an integral part of the outer wound cover. In addition, this type of single piece dressing may have flexible risers to lift the central portion of the dressing away from the wound for the purpose of allowing fluid flow to reach the entry port of the wound drainage tube. This type of dressing does not provide for packing the wound so that it can heal from bottom up. Likewise, it does not provide any method of distributing medications or antibiotic preparations to the wound. It would be desirable to have a wound dressing system which provides for packing a wound to facilitate its healing from the bottom up.

While addressing the basic need to protect wounds during the healing process, the prior art has failed to provide a wound treatment system which packs the wound, which provides inputs for preparations to be applied to the wounds, which drains exudates from the wounds, and which seals the area of the wound to prevent both contamination of the wound and/or contamination of the area outside of the dressing due to leakage from the wound dressing.

SUMMARY OF THE INVENTION

The present invention solves the foregoing problems by providing a portable closed wound drainage system ("CWDS") which includes a pouch shaped dressing that is inserted into a wound, tubing which is secured inside the pouch at one end, and secured to the other end of the tubing, a drain/suction unit. The pouch is fabricated from porous material that is permeable to body fluids, can be made in any suitable size and shape that is suitable for a particular wound size and shape. The pouch contains porous material, and may optionally contain beads and fillers which are antibacterial in nature. The tubing can have a single or multi-lumen structure. The tubing is fabricated from flexible material with perforations in the walls of the distal portion of the tubing which, when the tubing is inserted in the pouch, will allow exudates to enter laterally. A portable drain/suction unit is attached to the other end of the tubing. The portable drain/suction unit is preferably a portable battery powered device. The pouch and the tube are sealed by a flexible sealing material which is applied to the outer surface of the skin around the periphery of the pouch and secured to the tubing and pouch where the tubing exits the pouch. This sealing material is preferably a hydro-colloid, a silicone, or a lyogel, such as a hydrogel, which are easily deformable.

DESCRIPTION OF THE PREFERRED EMBODIMENT

Figure 1A:
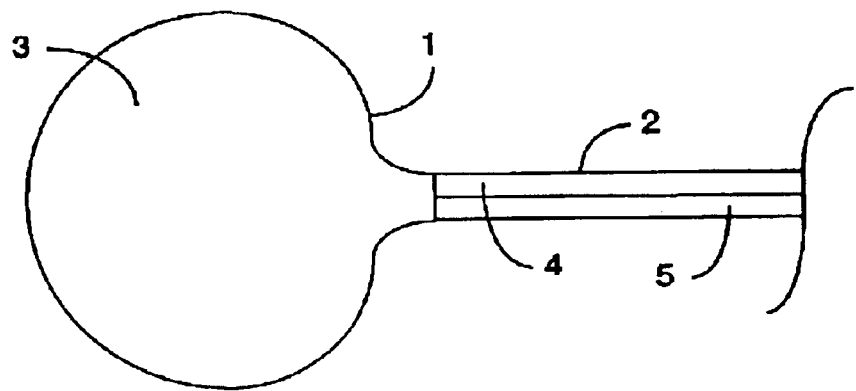
FIG. 1A is a top view of a preferred embodiment of the pouch with a multiple lumen section of tubing inserted in the pouch.

Prior to a detailed discussion of the figures, a general overview of the CWDS system will be presented. The CWDS system is designed to be used as a suction therapy device based on VAC principles. The invention disclosed herein improves upon NPT and VAC systems in that it greatly increases the comfort and mobility of patients, it allows dressings to be applied more rapidly and with less pain, and it allows antibacterial steps to be taken in regard to a wound without removing the dressing.

In general, negative pressure therapy is usually painful to the patient when it is used to treat a wound area. With existing procedures, the patient experiences pain when prior art foam or similar types of dressing material are placed inside an open wound. This is especially true since prior art dressings often require multiple attempts to install them in a wound. In addition, the sealing of the wound area with a surgical drape and the placement of the suction head attachment also causes patient discomfort and pain. In addition to the discomfort and pain to the patient, this type of dressing often requires greater expense because the therapy administrator may need an assistant in order to apply the surgical drape properly. Commercially available surgical drapes typically have a strong adhesive backing, and a thin layer of fitness. Maneuvering this type of drape requires substantial practice to install properly. As a result, patients are often in severe pain as a result of multiple trial and error attempts to install these drapes.

The CWDS is designed to eliminate much of the discomfort and pain of having a dressing installed in a wound. The soft and flexible nature of the pouch (discussed below) allows it to be inserted in minimal time and with minimal discomfort to the patient. Its deformable shape allows it to completely fill the wound cavity. Likewise, the gel seal (also discussed below) is comfortably installed without any of the trial and error related to conventional drapes. The CWDS dressing disclosed herein can be used in conjunction with NPT, VAC, or other systems.

Because of the soft structure of the CWDS dressing, it is conformable to body cavities, wound cavities, and to shallow surface wounds. Since it can be formed as a relatively flat dressing, it is also capable of use in drainage of skin surface conditions, such as surgical and nonsurgical wounds, donor or skin graft recipient sites, and/or areas of dehiscence of surgical wounds.

There are five main components of the CWDS system. They are the pouch, the tubing, the drain/suction unit, the sealant, and the protective cover.

The first component is the pouch dressing. The outer surface of the pouch is made from a soft flexible porous material. It is permeable to fluids and exudates. The outer surface of the pouch contains numerous small perforations or pores which allow exudates to enter the pouch and which allow suction from the drain/suction device to act on the exudates. Because it is soft and pliable, it can be installed by medical personnel to snugly fit within a wound cavity. When placed inside the wound cavity, fluids and exudates in the wound pass through the outer surface of the pouch and are absorbed by porous material inside the pouch. Later, the exudates are drawn out through the tubing for disposal. In the preferred embodiment, the pouch is formed in either tubular or flat configurations. However, those skilled in the art will recognize that the pouch can be formed in any suitable shape or size. For example, pouches can be flat, spherical, tubular, irregular, etc. The only requirement as to shape and size is that the pouch is suitable to treat a particular size and shape of wound.

Another optional feature of the pouch is that it can be formed such that it provides active treatment of bacterial agents. For example, the pouch can be used as a means to deliver medications, such as antibiotics, which are pumped into the pouch via the tubing. The pouch normally contains beads or fillers. They can be loose, or secured around the tubing inserted in the pouch. The filler can be any antimicrobial material or equivalent. If the filler in the pouch is impregnated with antibiotics or other medications, they can leak into the wound area to assist healing in addition to destroying infectious material encountered inside the pouch. The shape of the beads/filler allows the pouch to be conformed to the shape of the wound. Further, at least some of the beads may be fabricated from material with known antibacterial properties, such as silver.

The pouch has a number of advantages over conventional dressings. It conforms to tissue contours, thereby avoiding the situation where an area of a wound is left to dry out or accumulate fluids. It is a self-contained single use device which is preferably made in inexpensive disposable form. It can be used in conjunction with other commercially available dressing materials, or can be adapted to work in combination with other commercially available dressings. The material used for the pouch is biocompatible. It may contain active, medications for drug delivery to wound site, it may contain conductive material to allow measurement of electrical parameters, it may deliver continuous proposed electromagnetic field therapy, and/or it may be used to provide low current electrical stimulation in conjunction with low temperature heat. It provides self-adherence when used with a sealant agent and a protective cover which may also function as a wound margin skin protectant. Because it fills the wound cavity, the pouch prevents pooling of exudates which would otherwise prevent or slow down the healing process. It is bidirectional in the sense that it provides for the drainage and removal of infectious material and fluids, as well as the delivery of wound therapy in the form of medications, electrical stimulus, etc. It can be used for continuous irrigation of fluids/gases, and other microbial contaminants as well as gentle removal of debris.

Other advantages of the invention over prior art devices include the ability to treat not only deep cavity wounds, which surface treatment devices cannot reach, but also to treat shallow surface wounds. It not only provides the ability to actively drain a wound, but it also is designed to actively deliver antibacterial agents. Likewise, it can even be constructed of materials that have natural antibacterial properties. Due to the soft, malleable properties of the pouch, it can be easily and snugly fit within wounds having a variety of shapes and conform to the shape of the wound so the entire wound cavity is filled. As can be seen, the CWDS system provides numerous benefits over commercially available systems.

The next important structure in the CWDS is the tubing. The tubing can be as simple as a single lumen device which only provides suction. However, in the preferred embodiment, it is a multi-lumen device which uses one lumen to apply vacuum pressure to the wound area, and a secondary lumen as a pathway to supply medications and/or antibacterial agents to the pouch for use in the wound healing process. Of course, multiple lumens may also be used for suction.

The tubing in the preferred embodiment is a single or dual line flexible tube which is fabricated from PVC or silicone based material. However, those skilled in the art will recognize that any suitable material may be used to fabricate the tubing, and will also recognize that the number of tubes chosen can vary, so long as they achieve the goals of the invention. For example, one lumen may be used to apply vacuum pressure, one lumen may be used to supply antibiotics, to irrigate a wound, or even to provide gases (e.g., oxygen) which may assist in healing the wound. In addition, a third lumen may be used to provide a path for an electrical line to provide electrical simulation to the wound.

Another important structural feature of the tubing is the manner in which suction is applied. While it is always possible to apply suction through a single opening in the distal end of the tubing (i.e., the end of the tube which is inside pouch), this approach may result in excessive force being applied to a small, localized area of the wound. In the preferred embodiment, a series of small perforations in the distal portion of the tubing are made to disperse the vacuum pressure in order to prevent the vacuum pressure from becoming too localized. The perforations are usually made in approximately the last inch of the tubing. In addition, the perforated section of the tubing is placed inside of the pouch, and the perforations extend longitudinally along the tubing wall. The number of perforations and their location in regard to one another is not critical and can vary. The only requirement is that they are large enough and are sufficient enough in number to facilitate fluid flow, and are sufficiently distributed in location to avoid localized vacuum pressure.

The drain/suction unit is another important part of the CWDS system. In the preferred embodiment, it is a portable, lightweight, battery operated, suction pump which attaches to the proximal end of at least one lumen of the tubing. Of course, other lumens may be attached to other items, such as antibiotic drip devices, electrical devices, etc.

In the preferred embodiment, the drain/suction unit is designed such that it can be easily carried by a shoulder attachment or by attachment to the belt of the patient. In addition to the vacuum pump, the drain/suction unit also preferably includes a reservoir, a battery power supply, and control switches for turning the drain/suction unit on or off.

In addition, the reservoir component should have a sensor alarm to notify the patient or the medical care provider when the reservoir is almost filled. It is an important advantage for the device to be portable so that patient will have the freedom to move about rather than being confined to a fixed location.

The sealant is the next important component of the CWDS system. In particular, once the pouch and tubing are inserted into, or on, the wound, it is important to seal the wound area such that contaminants cannot enter the wound area from the outside and also to prevent exudates from leaking out of the CWDS where they may create an infection hazard to others. Prior art devices typically use dressing covers which are taped or adhered to the patients skin such that the dressing cover forms a sealed cover which prevents leakage. Particular care must be used with this type of dressing around the area where the tubing exits the dressing. Extra time and effort must be taken to ensure that there are no leaks in the area the tubing. Further, prior art dressings tend to pull away from the skin when the patient is mobile.

In the preferred embodiment, the sealant is a flexible gel which is applied over the top of the pouch after it is placed inside the wound. The gel forms an impermeable seal which prevents leakage in either direction (e.g., leakage is intended to mean not only exudate leakage from the wound, but also air leakage from outside the dressing). By sealing the dressing with the gel, the environment surrounding the wound becomes more stable. In particular, both moisture and temperature will be more stable, which in turn facilitates the healing process. In addition, another significant advantage of the gel is that it is flexible and allows the patient to move about without breaking the seal between the patient's skin and the gel. This improves upon taped dressing covers which frequently detach from the patient's skin when the patient is moving.

The protective cover is the final major component of the CWDS system. Once the dressing is secured in place by the gel, a protective cover is placed over the dressing and gel. The protective cover performs several functions. Its primary function is to protect the sealant from dirt. In addition, it also helps to ensure that the sealant remains in contact in and around the pouch and the wound area. It helps reduce the possibility of friction or sheer when the patient is mobile. And finally, it is used for cosmetic reasons to cover the wound area.

The invention provides several advantages over the prior art. The closed wound dressing system allows a medical care provider to pack a wound with a dressing which, due to its soft and flexible nature, can be conformed to the shape of the wound and be used to pack a wound with a minimum amount of pain or discomfort to a patient. Because it conforms to the shape of the wound, the medical care provider does not have to spend time adjusting the size of the dressing to fit a particular shape wound which results in faster application of the dressing. Once the dressing is inserted into the wound, it provides a vehicle for delivering medications, such as antibiotics, to the wound area without having to open the dressing. The pouch is structured such that it can simultaneously deliver medications, actively combat bacteria with components fabricated from antibacterial materials, and drain a wound to facilitate rapid healing. In addition, the use of a flexible gel seals the wound area and allows a patient to engage in activities without restriction during the healing process. In the preferred embodiment, the flexible gel sealing material is a hydro-colloid, a silicone, or a lyogel, such as a hydrogel, which are all easily deformable.

Having described the invention in general, we turn now to a more detailed discussion of the figures.

In FIG. 1A, a top view of a preferred embodiment of the pouch 1 is shown. The upper surface 3 of the pouch 1 is intended to be made with a nonporous material to prevent any leakage of exudates from the wound, through the pouch 1, to the outside of the dressing where it may cause contamination of others. The upper surface 3 of the pouch 1 can be made with any suitable material so long as it retains its flexibility and prevents leakage of exudates through the upper surface 3. For ease of illustration, the shape of the pouch 1 is shown as having a generally circular structure. Those skilled in the art will recognize that since the pouch 1 is intended to be a flexible and malleable device which is conformed to the shape of a patient's wound, the exact shape of the pouch 1 is not critical and may vary in both size and shape.

Also shown in this figure is a section of tubing 2. The tubing 2 is shown with its distal end inserted into the pouch 1. The proximal end (shown below in regard to FIG. 6) of the tubing 2 is attached to the drain/suction unit (also shown in regard to FIG. 6). The purpose of the tubing 2 is to provide vacuum pressure to withdraw exudates, debris, dead cells, etc., through the tubing 2 for disposal. The tubing 2 is also intended to be sufficiently flexible such that the portion inside the pouch 1 can be easily bent when the pouch 1 is being folded or shaped to conform to the shape of a wound cavity. Likewise, the portion of the tubing 2 which is outside of the pouch 1 needs to be flexible to allow it to be manipulated to suit a particular wound and a particular patient. In the preferred embodiment, the tubing 2 is fabricated from PVC or silicone tubing similar to that used for commercially available catheter tubes. However, any material can be used to fabricate the tubing 2 so long as it is suitable for the intended purposes of the CWDS.

More than one lumen can be used by the tubing 2 as illustrated by the multiple lumen section of tubing 2 inserted in the pouch 1. In this figure, a primary lumen 4 and a secondary lumen 5 are shown as part of the tubing 2. While the invention can work satisfactorily with a single lumen which is used to provide vacuum pressure, the preferred embodiment envisions multiple lumens. For example, primary lumen 4 provides vacuum pressure to withdraw exudates from the wound cavity, and through the pouch 1, for external disposal. In addition, secondary lumen 5 is available to perform other functions, such as delivery of medications to the pouch 1 and wound area, and delivery of gases to the pouch 1 and wound area. It also provides a path for insertion of other devices, such as electrical conductors which are used to provide low-level electrical stimulus or heat for treatment of a wound area, or other measurement or treatment devices. Of course, more than two lumens can be used depending on the nature of treatment.

Figure 1B:
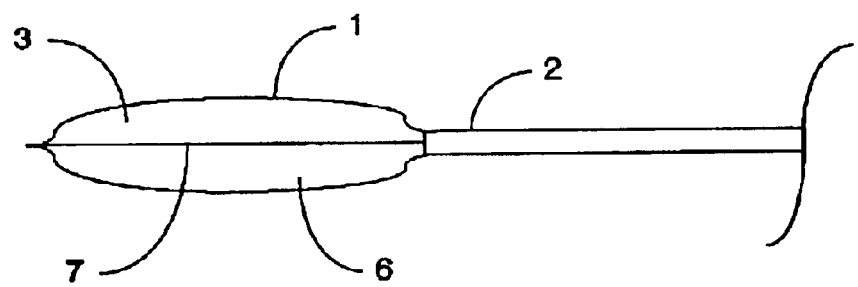
FIG. 1B is a side view of a preferred embodiment of the pouch with a section of tubing inserted into the pouch.

FIG. 1B illustrates a side view of the preferred embodiment of FIG. 1A. In this figure, the pouch 1 is shown with a section of tubing 2 inserted into it. Also shown in this figure is the lower surface 6 of the pouch 1. As noted above, the upper surface 3 is intended to be nonporous to prevent exudates from leaking out of the pouch 1. However, the lower surface 6 of the pouch 1 is intended to be porous to allow exudates and other material from the wound cavity to be absorbed into the pouch 1 from which it can be later removed and discarded. The upper surface 3 and the lower surface 6 are joined at seam 7 to form a pouch structure with an internal chamber which holds filler.

Figure 1C:
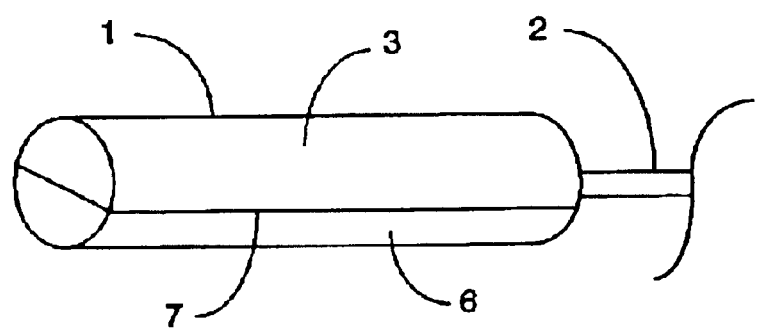
FIG. 1C is a perspective view of an alternative preferred embodiment of the pouch showing a generally tubular shaped pouch structure.

A perspective view of an alternative preferred embodiment is shown in FIG. 1C. In this embodiment, the pouch 1 is shown as having a generally tubular shaped pouch structure. This figure is intended to illustrate the fact that the actual shape of the pouch 1 is only important in that it should be convenient to insert into a wound cavity. Therefore, the pouch 1 may have any convenient shape or size, so long as it is compatible with the shape or size of a particular wound. This figure also illustrates a pouch 1 with an upper surface 3 and a lower surface 6. Those skilled in the art will recognize that in the event a pouch 1 is to be placed entirely inside a wound cavity, is also possible to provide a pouch 1 in which the entire outer surface is porous and there is no upper surface 3.

Figure 2:
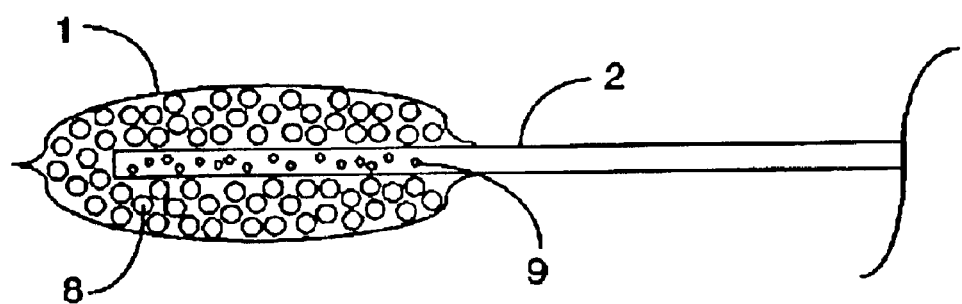
FIG. 2 is a side cutaway view of a preferred embodiment of the pouch which illustrates the pouch with a perforated section of tubing inserted inside, and beads which are used as pouch filler.

In regard to FIG. 2, this figure is a side cutaway view of a preferred embodiment of the pouch 1. As shown in this figure, the distal end of tubing 2 is inserted inside the pouch 1. A series of perforations 9 are arranged along the distal end of the tubing 2. The perforations 9 allow vacuum pressure to be applied by the tubing 2 across a wide area of the tubing 2 which is inserted into the pouch 1. By using the perforations 9, the vacuum pressure is distributed over a wider area and results in a reduced chance that pressure would be applied to a small local area. As a result, exudates are pulled from a wider area of the interior of pouch 2, rather than from a small area at the distal end of the tubing 2. Of course, to ensure that the vacuum pressure is distributed through perforations 9, the distal end of tubing 2 is sealed.

Also shown in this figure are beads 8 which are used as pouch 1 filler. Because of the shape of the beads 8, they allow the shape of the pouch 1 to be more easily manipulated for insertion into a particular shaped wound cavity. In addition, they also allow exudates and other undesirable materials to move through the interior of the pouch 1 without becoming snagged inside the pouch 1.

The filler in the pouch 1 can be made from a variety of materials. For example, the beads 8 can be fabricated from silver which has known antimicrobial characteristics. In addition, they can be made from a variety of other materials which may be actively antimicrobial, or neutral, such as hydro foam, etc. In a multi-lumen embodiment, such as that shown in regard to FIG. 1A, the primary lumen 4 may be extracting exudates under vacuum pressure while a secondary lumen 5 may be used to inject medications, etc. into the internal cavity of the pouch 1.

Figure 3:
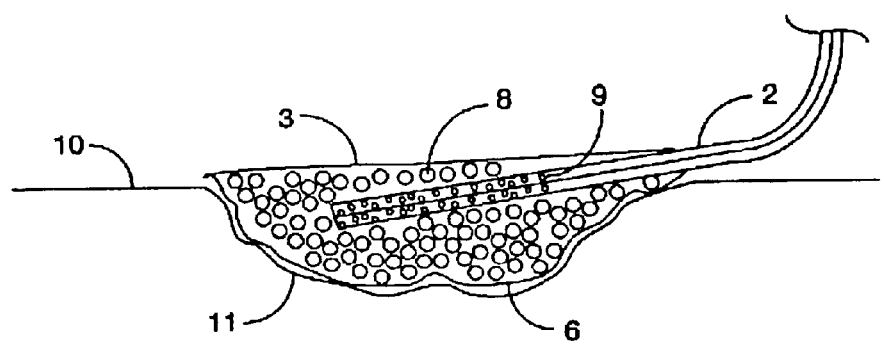
FIG. 3 is a side cutaway view of a preferred embodiment of the pouch which illustrates the pouch inserted within a wound cavity.
Figure 4:
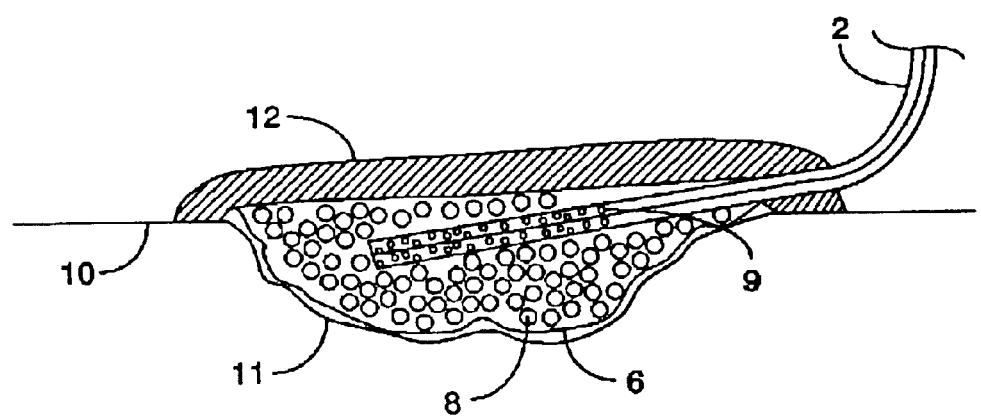
FIG. 4 is a side cutaway view of a preferred embodiment of the pouch secured inside the wound cavity by flexible gel, and with tubing extending through the flexible gel.
Figure 5:
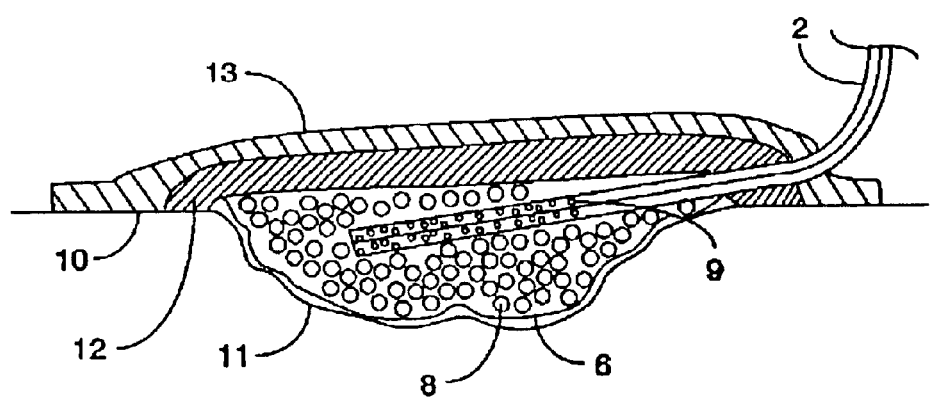
FIG. 5 is a side cutaway view of a preferred embodiment of the pouch secured inside the wound cavity by flexible gel, and with an external drape covering the gel and the wound area.

FIGS. 3–5 together illustrate how the pouch 1 is installed in a wound cavity 11 (shown in FIG. 3) when the CWDS system is used. The first step is illustrated in FIG. 3 which shows the pouch 1 installed within the wound cavity 11. The next step is the installation of the gel 12 which seals the wound. This step is illustrated in FIG. 4. After the gel 12 is installed, the next step is to install a cover 13 over the gel 12. This step is illustrated in FIG. 5. The cover protects the gel 12 from damage, and in addition, provides a cosmetic cover.

In regard to FIG. 3, a side cutaway view of a preferred embodiment of the pouch 1 is shown which illustrates the pouch 1 inserted into a wound cavity 11. The healthy section of the patient's skin surface 10 is also illustrated. This figure illustrates a significant advantage of the invention in that since the pouch 1 is flexible and can be conformed to the shape of a wound 11, the entire area of the wound 11 cavity can be properly treated by the CWDS system. In dressing systems which use a wound cover that is fixed in size and shape, there may be areas which are not properly drained due to the inability of that dressing system to provide adequate vacuum pressure to a particular portion of the wound. Also illustrated in this figure is the upper surface 3 which prevents exudates from leaking out of the pouch 1, which results and their being held in the pouch 1 until they are eventually pulled through the perforations 9 and withdrawn from the pouch 1 under vacuum pressure.

In FIG. 4, a side cutaway view of the preferred embodiment of FIG. 3 is shown. In this figure, the pouch 1 is secured inside the wound cavity 11 by flexible gel 12. When the flexible gel 12 is applied, it is in a viscous state which allows it to cover the pouch area from sections of healthy skin 10, and in addition, it can also seal the tubing 2 which extends through the flexible gel 12. A suitable gel 12 must have flexibility to prevent it from detaching from the skin 10 if the patient is mobile. In addition, it must be easily deformable prior to being set to allow it to cover a particular size pouch 1 and wound 11. It should be substantially impermeable to prevent contaminants from entering the wound cavity 11 and also to prevent exudates from escaping the wound cavity 11 and dressing. In the preferred embodiment, a variety of commercially available gels can be used, such as hydro-colloids, silicones, or a lyogel, such as a hydrogel. In addition to those listed, any suitable material can be used as the gel 12 as long as it accomplishes the purposes and goals of the invention.

Regarding FIG. 5, this figure shows a side cutaway view of a preferred embodiment of the pouch 1 which is secured inside the wound cavity 11 by flexible gel 12, and then by an external drape 13 which covers the gel 12 and the wound area. The external drape 13 is applied in the same manner that an external drape is typically applied to a wound. The external drape 13 acts as a protective cover which performs several functions. Its most important function is to protect the gel 12 from dirt and damage. In addition, it helps the gel 12 to remain in contact both with the pouch 1, and with the skin 10 surrounding the wound area. By adding extra support, it reduces the possibility of friction or sheer when the patient is mobile. It also provides esthetic value by providing a cosmetic cover for the wound area and CWDS system. It is not as critical that the seal joining the external drape 13 to the patient's skin 10 is perfect since the isolation of the wound from the external environment is performed by the gel 12.

As can be seen from the foregoing, the installation of the pouch 1 in a wound cavity 11 is a relatively easy procedure. The pouch 1 can be rapidly and easily inserted into a wound cavity 11, and conformed to the shape of the wound cavity 11. The viscous nature of the gel 12 allows it to be rapidly and easily installed without the pain and discomfort associated with prior art drapes. Finally, the external drape 13 can be easily applied without the necessity for precision and re-installation which often happens with prior art drapes. Once the pouch 1 is installed in this manner, the CWDS system is ready to begin withdrawing exudates from the wound on a continuous basis.

Figure 6:
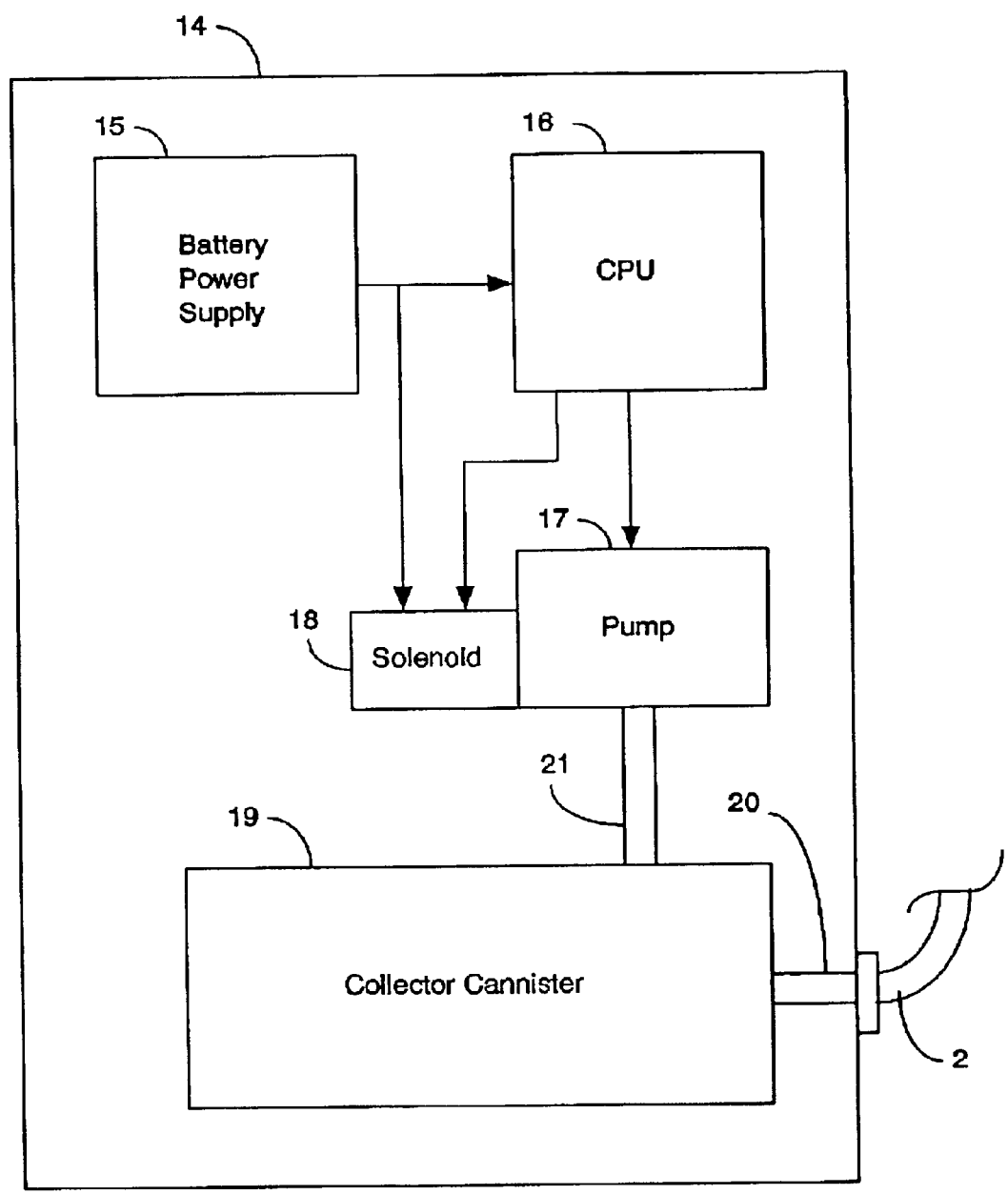
FIG. 6 is a block diagram illustrating the components of the drain/suction unit. Also shown is a section of tubing attached to the drain/suction unit.

FIG. 6 is a block diagram which illustrates the components of the drain/suction unit 14. The drain/suction unit 14 has several components. A power supply 15 is provided to power the various components of the device. In the preferred embodiment, the drain/suction unit 14 is battery operated to provide patient mobility. A CPU 16 controls the various functions of the device and allows the patient or medical care provider to turn on and off various functions such as the application of vacuum or the injection of medication. For ease of discussion, electronic control circuitry is referred to as CPU 16. However, CPU 16 may be a microprocessor, controller, or specialized fixed purpose circuitry, etc. Its only requirement is that it be able to control the various functions of the CWDS system. Also shown in this figure is the pump 17 which provides vacuum pressure to the pouch 1. The exudates pulled through the tubing 2 by the vacuum pressure would first be pulled into the drain/suction unit 14 at entry conduit 20. The exudates would enter the collection canister 19 from entry conduit 20 where they would be trapped. The vacuum pressure is applied to the collection canister 19 via conduit 21 that is attached to pump 17. Pump 17 may also be turned on and off under control of CPU 16 by solenoid 18. Those skilled in the and the art will recognize that some of these components can be merged together. Therefore, this figure is intended to illustrate functions provided by the drain/suction unit 14, and not necessarily the discrete components used to fabricate it.

As can be seen from the foregoing, the CWDS system presented herein provides a number of advantages over the prior art. In particular, it provides a soft flexible system which can be installed within the wound in a rapid manner, and with minimal attempts to position the pouch 1. This results in a substantial reduction in pain and discomfort experienced by patients as compared to the installation of prior art dressings. The ease of installation also allows the single medical care provider to install the dressing without requiring assistance from second party. The beads 8 provide active antimicrobial treatment of wounds which accelerates the healing process. In addition, the shape and the flexibility in the structure of the pouch 1 allows the pouch 1 to be in contact with the entire wound cavity which increases drainage capability and healing speed. The multi-lumen tubing 2 allows the delivery of medications without disturbing the wound dressing. The use of a nonporous upper surface 3 in combination with a porous lower surface 6 in the pouch 1 allows exudates to be pulled into the pouch 1 without subsequent leaking to the outer surface of the pouch 1. The structure of the tubing and the location of the perforations further provides a dispersed vacuum pressure which improves the process of removing exudates from the wound area which in turn increases the rate of healing. As a result, the invention provides a combination of benefits in a single wound treatment system which is not found in any alternative treatment devices.

While the invention has been described with respect to a preferred embodiment thereof, it will be understood by those skilled in the art that various changes in detail may be made therein without departing from the spirit, scope, and teaching of the invention. For example, the material used to construct the pouch and tubing may be anything suitable for its purpose, the size and shape of the beads and their composition can vary, etc. Accordingly, the invention herein disclosed is to be limited only as specified in the following claims.

What is claimed is:

1. A closed wound dressing system comprising:
   a pouch having a continuous, outer surface, at least portion of which is porous, the outer surface of the pouch forming an inner chamber having filler capable of holding exudates entering the chamber through the porous outer surface, the pouch further being flexible and conformable such that its external shape will conform to a wound cavity when the pouch is inserted into the wound cavity;
   tubing having an inner conduit, a distal end and a proximal end, the tubing further having input means to accept exudates drawn into the tubing under vacuum pressure; and
   a vacuum pump attached to the proximal end of the tubing, the vacuum pump applying vacuum pressure to the tubing;
   whereby a wound cavity can be substantially filled by a porous conformable pouch which applies vacuum pressure to remove exudates from the wound.

2. A system, as in claim 1, wherein the filler is at least partially comprised of beads, the beads further having a shape which will conform to movement inside the pouch; whereby the beads do not interfere with conforming the shape of the pouch to a wound cavity.

3. A system, as in claim 2, wherein the beads have antimicrobial characteristics.

4. A system, as in claim 3, wherein at least a portion of the beads are fabricated from silver.

5. A system, as in claim 3, wherein the distal end of the tubing further comprises a plurality of perforations, the perforations sized such that exudates can be drawn from the pouch into the tubing under vacuum pressure.

6. A system, as in claim 1, further comprising: a layer of gel, the gel applied to an upper surface of a wound area and the pouch such that the wound area and the pouch are substantially isolated from the external environment.

7. A system, as in claim 6, wherein the gel is formulated from at least one material selected from the group consisting of hydro-colloids, silicones, lyogels and hydrogel.

8. A system, as in claim 7, further comprising:
an external drape, the external drape sized such that when applied to the area of the wound, it covers the entire wound area and the pouch, the external drape further attached to the wound area at its periphery.

9. A system, as in claim 1, wherein the distal end of the tubing further comprises a plurality of perforations, the perforations sized such that exudates can be drawn from the pouch into the tubing under vacuum pressure.

10. A system, as in claim 9, wherein the tubing further comprises at least a first and second lumen, at least one of the lumens being used to apply vacuum pressure to the pouch.

11. A system, as in claim 10, wherein the first lumen applies vacuum pressure to the pouch, and the second lumen is used to deliver medication to the pouch.

12. A system, as in claim 10, wherein the first lumen applies vacuum pressure to the pouch, and the second lumen applies electrical stimulation to the pouch.

13. A system, as in claim 10, further comprising:
a layer of gel, the gel applied to an upper surface of a wound area and the pouch such that the wound area and the pouch are substantially isolated from the external environment.

14. A system, as in claim 13, further comprising:
an external drape, the external drape sized such that when applied to the area of the wound, it covers the entire wound area and the pouch, the external drape further attached to the wound area at its periphery.

15. A system, as in claim 1 wherein the pouch is secured inside of the wound cavity with a layer of gel applied to the pouch and an upper surface of a wound area.

16. A method of draining wounds, comprising:
inserting a conformable pouch into a wound cavity such that the pouch substantially fills the cavity and remains in close proximity with the surface of the wound, the pouch having a continuous, external surface, the external surface of the pouch forming an internal cavity of the pouch;
applying vacuum pressure to the internal cavity of the pouch such that the vacuum pressure is distributed over a substantial portion of the pouch; and
making at least portion of the pouch porous such that exudates from the wound enter the pouch when vacuum pressure is applied;
whereby the conformable pouch remains in contact with a substantial surface area of the wound and provides vacuum drainage to a substantial surface area of the wound.

17. A method, as in claim 16, including the additional step of filling the internal cavity with filler, at least a portion of the filler being beads.

18. A method, as in claim 17, including the additional step of sealing the pouch and the wound area with a flexible gel.

19. A method, as in claim 18, including the additional step of providing an external cover over the wound and over the gel covering the pouch;
whereby the pouch and the wound are protected from the external environment.

20. A method, as in claim 16, including the additional step of providing a conduit to inject medication into the pouch;
whereby medication can be inserted into a sealed wound dressing.

21. A closed wound dressing system comprising:
a pouch having an outer surface, at least portion of which is porous, and an inner chamber having filler capable of holding exudates entering the chamber through the porous outer surface, the pouch further being flexible and conformable such that its external shape will conform to a wound cavity when the pouch is inserted into the wound cavity, the filler is at least partially comprised of beads, the beads further having a shape which will conform to movement inside the pouch, whereby the beads do not interfere with conforming the shape of the pouch to a wound cavity;
tubing having an inner conduit, a distal end and a proximal end, the tubing further having input means to accept exudates drawn into the tubing under vacuum pressure; and
a vacuum pump attached to the proximal end of the tubing, the vacuum pump applying vacuum pressure to the tubing;
whereby a wound cavity can be substantially filled by a porous conformable pouch which applies vacuum pressure to remove exudates from the wound.

22. A system, as in claim 21, wherein the beads have antimicrobial characteristics.

23. A system, as in claim 21, wherein the distal end of the tubing further comprises a plurality of perforations, the perforations sized such that exudates can be drawn from the pouch into the tubing under vacuum pressure.

24. A system, as in claim 21, further comprising:
a layer of gel, the gel applied to an upper surface of a wound area and the pouch such that the wound area and the pouch are substantially isolated from the external environment.

25. A closed wound dressing system comprising:
a pouch having an outer surface, at least portion of which is porous, and an inner chamber having filler capable of holding exudates entering the chamber through the porous outer surface, the pouch further being flexible and conformable such that its external shape will conform to a wound cavity when the pouch is inserted into the wound cavity;
a layer of gel, the gel applied to an upper surface of a wound area and the pouch such that the wound area and the pouch are substantially isolated from the external environment;
tubing having an inner conduit, a distal end and a proximal end, the tubing further having input means to accept exudates drawn into the tubing under vacuum pressure; and
a vacuum pump attached to the proximal end of the tubing, the vacuum pump applying vacuum pressure to the tubing;

whereby a wound cavity can be substantially filled by a porous conformable pouch which applies vacuum pressure to remove exudates from the wound.

26. A system, as in claim 25, wherein the gel is formulated from at least one material selected from the group consisting of hydro-colloids, silicones, lyogels and hydrogel.

27. A method of draining wounds comprising:

inserting a conformable pouch having an external surface and an internal cavity into the wound cavity, such that the pouch substantially fills the cavity and remains in close proximity with the surface of the wound;

filling the internal cavity with filler, at least a portion of the filler being beads;

applying vacuum pressure to the internal cavity of the pouch such that the vacuum pressure is distributed over a substantial portion of the pouch; and making at least portion of the pouch porous such that exudates from the wound enter the pouch when vacuum pressure is applied;

whereby the conformable pouch remains in contact with a substantial surface area of the wound and provides vacuum drainage to a substantial surface area of the wound.

28. A method, as in claim 27, including the additional step of sealing the pouch and the wound area with a flexible gel.

29. A method of draining wounds comprising:

inserting a conformable pouch having an external surface and an internal cavity into the wound cavity, such that the pouch substantially fills the cavity and remains in close proximity with the surface of the wound;

applying vacuum pressure to the internal cavity of the pouch such that the vacuum pressure is distributed over a substantial portion of the pouch; and making at least portion of the pouch porous such that exudates from the wound enter the pouch when vacuum pressure is applied;

whereby the conformable pouch remains in contact with a substantial surface area of the wound and provides vacuum drainage to a substantial surface area of the wound;

providing a conduit to inject medication into the pouch, whereby the medication can be inserted into a sealed wound dressing.

30. A method, as in claim 29, including the additional step of sealing the pouch and the wound area with a flexible gel.

* * * * *

UNITED STATES PATENT AND TRADEMARK OFFICE
CERTIFICATE OF CORRECTION

PATENT NO. : 6,979,324 B2
APPLICATION NO. : 10/243004
DATED : December 27, 2005
INVENTOR(S) : Farhad Bybordi et al.

It is certified that error appears in the above-identified patent and that said Letters Patent is hereby corrected as shown below:

Under References Cited, on Page 2, under U.S. Patent Documents, please insert -- 3,826,254 A 7/1974 Mellor --;

Under References Cited, on Page 2, under U.S. Patent Documents, reference no. 22, please delete "3,874,687" and insert -- 3,874,387 --;

Under References Cited, on Page 4, under Other Publications, reference no. 1, please delete "to" and insert -- of --;

Under References Cited, on Page 5, under Other Publications, column 2, reference no. 2, please delete "Unfallchirug" and insert -- Unfallchirurg --;

Under References Cited, on Page 5, under Other Publications, column 2, reference no. 3, please delete "Ginekilogija" and insert -- Ginekologija --;

UNITED STATES PATENT AND TRADEMARK OFFICE
CERTIFICATE OF CORRECTION

PATENT NO.         : 6,979,324 B2
APPLICATION NO. : 10/243004
DATED                : December 27, 2005
INVENTOR(S)      : Farhad Bybordi et al.

It is certified that error appears in the above-identified patent and that said Letters Patent is hereby corrected as shown below:

Under References Cited, on Page 6, under Other Publications, column 1, reference no. 10, after "A new dressing" insert -- method --;

Under References Cited, on Page 6, under Other Publications, column 2, reference no. 2, please delete "Garcia-Rinald" and insert -- Garcia-Rinaldi --;

Under References Cited, on Page 6, under Other Publications, column 2, reference no. 22, please delete "Lousi" and insert -- Louis --.

Signed and Sealed this

Seventeenth Day of October, 2006

JON W. DUDAS
*Director of the United States Patent and Trademark Office*